(12) United States Patent
Paoluccio et al.

(10) Patent No.: US 7,650,885 B2
(45) Date of Patent: Jan. 26, 2010

(54) MOUTHPIECE AND MASK FOR VENTILATION ASSISTANCE AND CONNECTOR FOR JOINING OBJECTS

(76) Inventors: John A. Paoluccio, 3530 Kleman, Modesto, CA (US) 95356; John J Paoluccio, 1820 Pennebaker, Apt. 270, Manteca, CA (US) 95336

( * ) Notice: Subject to any disclaimer, the term of this patent is extended or adjusted under 35 U.S.C. 154(b) by 383 days.

(21) Appl. No.: 10/861,752

(22) Filed: Jun. 3, 2004

(65) Prior Publication Data
US 2005/0268914 A1 Dec. 8, 2005

(51) Int. Cl.
*A62B 18/02* (2006.01)
*A62B 18/08* (2006.01)

(52) U.S. Cl. .............. 128/206.29; 128/205.25

(58) Field of Classification Search ............ 128/201.26, 128/205.25, 206.27, 206.29, 848, 202.27; 602/902; 433/69, 68, 71, 73, 72, 214, 213
See application file for complete search history.

(56) References Cited

U.S. PATENT DOCUMENTS

| | | | | |
|---|---|---|---|---|
| 1,589,802 A * | 6/1926 | Gould | ......................... | 433/73 |
| 3,037,501 A * | 6/1962 | Miller | ................... | 128/206.29 |
| 3,809,079 A * | 5/1974 | Buttaravoli | ............ | 128/206.24 |
| 4,470,413 A * | 9/1984 | Warncke | ................ | 128/201.18 |
| 4,719,911 A * | 1/1988 | Carrico | ................... | 128/206.29 |
| 5,078,600 A * | 1/1992 | Austin | ......................... | 433/73 |
| 5,197,463 A * | 3/1993 | Jeshuran | ................ | 128/207.14 |
| 5,626,128 A * | 5/1997 | Bradley et al. | ......... | 128/200.26 |
| 5,752,510 A * | 5/1998 | Goldstein | ............. | 128/207.18 |
| 5,871,011 A * | 2/1999 | Howell et al. | .......... | 128/206.22 |
| 5,941,246 A * | 8/1999 | Roopchand | ............ | 128/207.14 |
| 5,983,892 A * | 11/1999 | Thornton | ............... | 128/201.26 |
| 6,012,455 A * | 1/2000 | Goldstein | ............. | 128/207.18 |
| 6,305,376 B1 * | 10/2001 | Thornton | .................... | 128/848 |
| 6,371,112 B1 * | 4/2002 | Bibi | ....................... | 128/204.18 |
| 6,374,824 B1 * | 4/2002 | Thornton | ............... | 128/201.26 |
| 6,606,991 B2 * | 8/2003 | Chou | .................... | 128/200.26 |
| 6,763,831 B2 * | 7/2004 | Sniadach | ............... | 128/206.29 |
| 6,789,543 B2 * | 9/2004 | Cannon | ................. | 128/207.18 |
| 6,860,270 B2 * | 3/2005 | Sniadach | ............... | 128/207.14 |
| 2005/0279355 A1 * | 12/2005 | Loubser | ................ | 128/200.26 |

* cited by examiner

*Primary Examiner*—Justine R Yu
*Assistant Examiner*—Kristen C Matter
(74) *Attorney, Agent, or Firm*—Robert S. Smith

(57) ABSTRACT

An apparatus for cooperation with associated ventilation apparatus which includes an engagement member for engaging and gripping a plurality of teeth of the user. The apparatus also includes an adjustment assembly for connecting the engagement member to associated ventilation apparatus. The adjustment assembly includes an elongated flexible member having a plurality of notches thereon and may further including a first discrete locking member and the elongated flexible member may have a bulbous axial extremity.

29 Claims, 6 Drawing Sheets

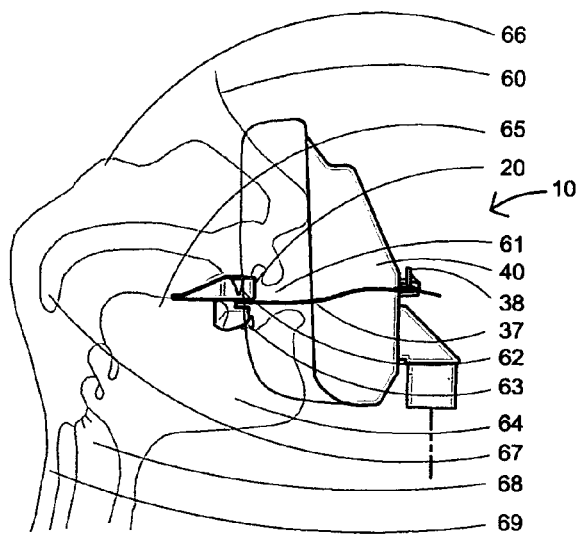
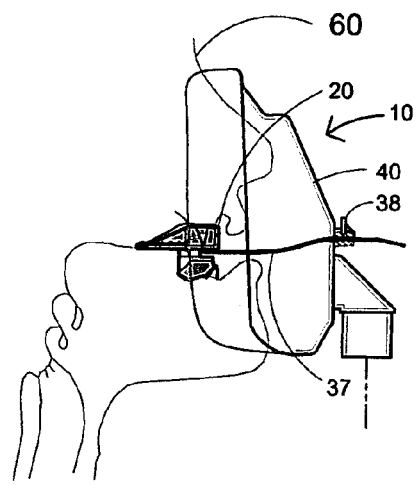
FIG. 2    FIG. 3
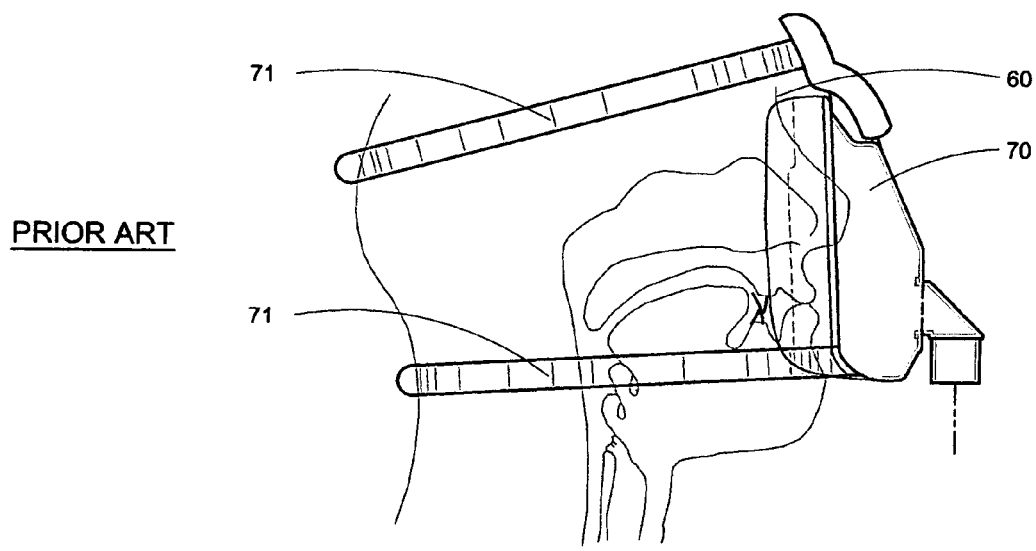
PRIOR ART
FIG. 4

MOUTHPIECE AND MASK FOR VENTILATION ASSISTANCE AND CONNECTOR FOR JOINING OBJECTS

BACKGROUND OF THE INVENTION

The invention relates to medical appliances and methods and particularly to apparatus and methods for ventilatory support which is also known as mechanical ventilation. The invention has application to respiratory assistance for both patients with and without snoring and or obstructive sleep apnea. Another aspect of the invention relates to apparatus and methods for joining or fastening objects. While the apparatus and method for joining is utilized in the medical appliance in accordance with present invention, it also has application to a wide variety of joining applications.

Mechanical ventilation or ventilatory support utilizes a machine that helps a patient breath. For most situations a masklike structure is attached over the patient's mouth and nose. (In emergency situations, which are not relevant to the present apparatus the patient has a tube inserted through the nose or mouth into the trachea (windpipe) which is attached to the ventilator. The insertion type devices are considered invasive types for very serious impaired patients and these methods are avoided where possible as damage may occur to the lining of the airway and throat.) The ventilator is a machine that can deliver a breath to a patient who may be having difficulty breathing or who may not be breathing at all. The breath frequency and the volume and/or pressure delivered by the ventilator during each breath are set on the machine. Typically, a respiratory therapist operates the ventilator. Often patients may need to be on a breathing machine either before, during, or after a heart operation or a procedure, such as a cardiac catheterization. Patients need to be mechanically ventilated at these times because they are given anesthesia or sedation that may suppress their own drive to breathe.

Often it is necessary to control breathing so the heart itself can rest. Occasionally, patients will be able to come off the ventilator prior to leaving the operating room. After surgery, most babies are connected to a ventilator. The length of time a patient remains on the ventilator depends on the severity of the cardiac defect and the type of surgical procedure performed. Patients receive sedation while they are on the ventilator. Sometimes patients will need arm or leg restraints. This is to prevent them from pulling out any tubes or intravenous catheters that they may have. When it is time to take the patient off the breathing machine, settings on the ventilator are turned down. This allows the patients to breathe more on their own. When patients are awake enough, the breathing tube is removed, and the ventilator is turned off. After the patients are off of the ventilator, they may need oxygen, delivered through two-pronged plastic tubing that fits into the nose.

The primary problem with this current technology is that the patient's airway sometimes closes or becomes partially restricted due to blockage of the airway from the tongue and or tissue in the back of the throat. This blockage frequently occurs when the lower jaw relaxes during sleep and drops back. This can case a lack of air to the patient's lungs and, in monitored patients, can trigger alarms to alert the medical staff of a problem. This can be very time consuming for the medical staff and dangerous to the patient.

With current ventilation methods and apparatus a mask is strapped to the patient and sometimes the patient's airway becomes restricted resulting in the patient not receive breathing air. In addition the straps and headgear used to attach the mask are very cumbersome and uncomfortable. Patients have heretofor been connected to a number of commercial type ventilator masks that are held in place with various straps and headgear. The primary problem with this current technology is that the patient's airway sometimes closes or becomes partially restricted due to blockage of the airway from the tongue and/or tissue at the back of the throat. This can case a lack of air to the patient's lungs and, in monitored patients, can trigger alarms that alert the medical staff to a problem. This can be very time consuming for the medical staff and dangerous to the patient.

Prior art methods and devices that allow ventilation air to be administered to a patient include full face masks, nasal masks, and insertion tubes of various sizes and shapes. All known prior art face masks are held in place by bulky and uncomfortable straps and headgear. If the patient has an obstructed or partially blocked airway as may occur if the patient has obstructive sleep apnea then no air or little air will reach the lungs of the patient resulting in adverse health effects or even death.

The costs associated with the related problems from present technology are very high. Patients frequently complain about the bulky and uncomfortable headgear and straps used to hold the mask in place. Adjustment is difficult and time consuming and re-adjustment is frequently necessary.

In an emergency where it is desired to release the mask quickly the straps can hinder the removal process. As the general population ages more patients need ventilation systems. The high costs associated with health care are a major economic problem. The prior art ventilation methods add significantly to these high costs of medical care.

Known fasteners include a wide variety of devices including screws and bolts. Many such fasteners are relatively expensive to manufacture, require relatively long time to assemble with objects being held together, do not allow quick release and/or require special equipment such as welding equipment.

SUMMARY OF THE INVENTION

An object of the present ventilation assistance invention is to provide a safe, effective, comfortable, unobtrusive means of administering ventilated air to a patient who may suffer from some sort of snoring or obstructive sleep apnea that may result in the blockage of the airway in the back of the throat.

Another object of the invention is to reduce the effect of tissue at the back of the patient's throat, thereby, helping to keep the patient's airway open for improved respiratory ventilation.

Still another object of the invention is to eliminate the need for bulky and uncomfortable straps and head gear and to thereby make the patient more comfortable.

Yet another object of the invention is to provide apparatus that can be used with most existing ventilator masks.

Another object of the invention is to provide apparatus that is compact.

A further object of the invention is to provide apparatus that after being custom fitted to the patient can thereafter be installed or removed in seconds.

Still another object of the invention is to substantially lower medical cost by eliminating the need for repetitive adjustments of straps and headgear as well as less monitoring and alarm activation occurrences.

An object of the fastener apparatus invention is to provide a very simple and inexpensive fastener apparatus and method for fastening.

Another object of the invention is to provide embodiments of a fastener and method of joining that allows rapid release.

A further object of this invention is to provide a fastener and method that can be very rapidly secured.

Still another object of the invention is to provide a method of joining an apparatus that does not require welding or soldering or other expensive apparatus to utilize.

It has now been found that these other objects of invention may be attained in a fastener apparatus for joining an associated first object having a first bore extending therethrough and a second object having a second bore extending therethrough which includes an elongated flexible member having a plurality of notches on a face thereof and first and second axial extremities; anchoring structure at the first axial extremity; and a first discrete locking member having a pawl and ratcheting mechanism dimensioned and configured for engagement with the plurality of notches.

In some forms of the apparatus the anchoring structure is a bulbous part of the elongated flexible member and in others it is a second discrete locking member. The first locking member may be releasable.

The invention includes apparatus for supporting an associated ventilation apparatus which includes an engagement member for engaging and gripping a plurality of teeth of the user; an adjustment assembly for connecting the engagement member to associated ventilation apparatus. The adjustment assembly includes an elongated flexible member having a plurality of notches thereon. The apparatus may further including a first discrete locking member and the elongated flexible member may have a bulbous axial extremity. The apparatus may further including a second discrete locking member. Each locking member may be releasable.

The invention also includes ventilation apparatus which includes a mask dimensioned and configured for engagement with a face; an engagement member for engaging and gripping a plurality of teeth of the user; and an adjustment assembly for connecting the engagement member to the ventilation apparatus. The adjustment assembly includes an elongated flexible member having a plurality of notches thereon.

In some cases the apparatus further includes a first discrete locking member and the apparatus may have an elongated flexible member that has a bulbous axial extremity. Some forms of the apparatus may include a second discrete locking member. The first locking member may be releasable. Some embodiments may include a ramp dimensioned and configured for mandible positioning. The engagement member may be a boil and bite formed product. In some cases the engagement member is at least partly formed of a polycarbonate resin material and lined with an ethylene vinyl acetate copolymer and terpolymer resin material.

The invention also includes the method for joining an associated first object having a first bore extending therethrough and a second object having a second bore extending therethrough which includes the steps of providing an elongated flexible member having a plurality of notches on a face thereof and first and second axial extremities; providing an anchoring structure at the first axial extremity; and providing a first discrete locking member having a pawl and ratcheting mechanism dimensioned and configured for engagement with the plurality of notches.

In some cases the method includes providing an anchoring structure that is a bulbous part of the elongated flexible member and the step of providing an anchoring structure includes providing a second discrete locking member and the step of providing a second locking member. In some cases the method includes the step of providing first locking member includes providing a locking member that is releasable.

The method also includes the method for supporting an associated ventilation apparatus that includes providing an engagement member for engaging and gripping a plurality of teeth of the user and providing an adjustment assembly for connecting the engagement member to associated ventilation apparatus including providing an elongated flexible member having a plurality of notches thereon.

In some cases the method further includes the step of providing a first discrete locking member, the step of providing and elongated flexible member includes providing an elongated flexible member having a bulbous axial extremity, the step of providing a second discrete locking member, and/or the step of providing a first locking member includes providing a first locking member that is releasable.

The invention also includes the ventilation method which includes providing. a mask dimensioned and configured for engagement with a face, providing an engagement member for engaging and gripping a plurality of teeth of the user, providing an adjustment assembly for connecting the engagement member to the ventilation apparatus, and the step of providing an adjustment assembly includes providing an elongated flexible member having a plurality of notches thereon.

In some cases this method includes the step of providing an adjustment assembly further includes providing a first discrete locking member, the step of providing an adjustment assembly includes providing an elongated flexible member that has a bulbous axial extremity, the step of providing an adjustment assembly further includes providing a second discrete locking member, the step of providing an engagement member includes providing a first locking member that is releasable, the step of providing an engagement member includes providing an engagement member that includes a ramp dimensioned and configured for mandible positioning, the step of providing an engagement member includes providing an engagement member that is a boil and bite formed product, the step of providing an engagement member includes providing an engagement member that is is at least partly formed of a polycarbonate resin material, and/or the step of providing an engagement member includes providing an engagement member that is lined with an ethylene vinyl acetate copolymer and terpolymer resin material.

BRIEF DESCRIPTION OF THE DRAWING

The invention will be better understood by reference the accompanying drawing in which:

FIG. 2 shows a schematic view of the device being fitted to a patient with the mask loose.

FIG. 3 shows a schematic view of the device as it is tightened against the patients face.

FIG. 4 shows a prior art ventilator mask with patient. Lower jaw is not moved forward.

DESCRIPTION OF THE PREFERRED EMBODIMENTS

The conventional cable tie is an elongated nylon product that is used to join bundles of cables or wires together as well as many other fastening means. A first end is provided with a locking channel or slip lock into which the second end is inserted. Axial movement of the second end into the locking channel proceeds in a manner similar to a ratchet whereby backward axial movement is not possible. This is sometimes referred to as a non-releasable rachet lock action. So-called releasable cable ties are provided with a mechanism that includes a release lever at the first end. The release lever allows the user to manually release the second end from the first end.

Figure 8:
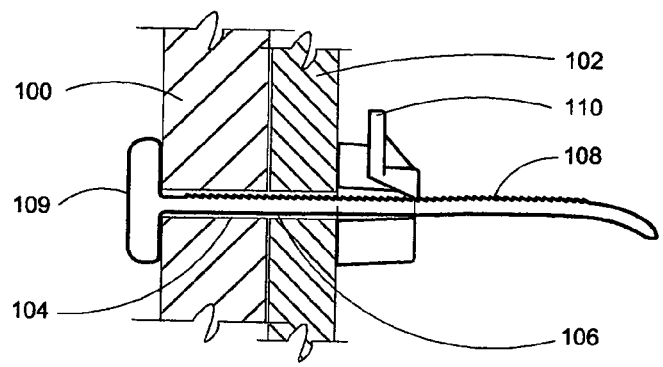
FIG. 8 illustrates, in an enlarged view, one embodiment of the fastener portion apparatus and method of this invention being used to hold two objects together. (This fastener could be used in place of a nut and bolt.)
Figure 9:
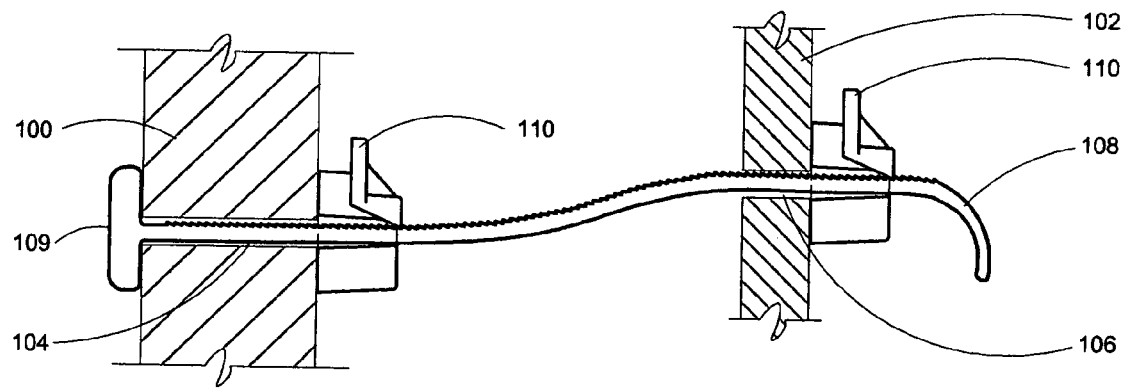
FIG. 9 is an enlarged view of the fastener portion of this invention being used to lock onto one object and holding another object. This view further includes a lock nut 110 disposed against the object or block 100.
Figure 10:
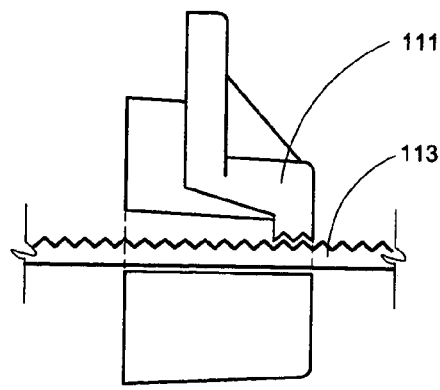
FIG. 10 is an enlarged view of the fastener portion of this invention with a different tie groove and lock design. This shape locks the part in place and prevents tie movement in either direction until the release lever is depressed. This contrasts with conventional cable ties that allow the tie to slip in one direction.

The present invention modifies a conventional releasable cable tie to provide a fastening mechanism and method for drawing two objects together and allowing selective release of the force that draws the two objects together. Referring now to FIGS. 8, 9, 10 the connector in accordance with present invention may be used to join two blocks of wood or other material 100, 102. The blocks of wood 100, 102 are provided with respective bores 104, 106. A prior art method of coupling-the two blocks of wood 100, 102 together would be to use a bolt and a nut (not shown). The same function can be achieved with a releasable cable tie 108 in accordance with the present invention that has a head 109 at a first axial extremity. The other axial extremity is inserted into the bores 104, 106 with the locking channel or slip lock 110 of the releasable cable tie 108 abutting a face of the block 100. In this case the locking channel 110 acts merely as a stop. An additional locking channel 110 is thereafter secured to the end of the first conventional releasable cable tie that was inserted into the bores 104, 106. Thereafter the user may grip the end of the first conventional releasable cable tie 108 that was inserted into the bores 104, 106 and pull the blocks of wood 100, 102 together. While a releasable cable tie is preferable for many applications, the invention also includes conventional non-releaseable cable tie assemblies. The description in this paragraph describes an embodiment with essentially two locking channels 110. Other embodiments will include a bulbous end 37a and a single slip lock or locking channel 110. The view of figure 10 show the pawl engagement with and an enlarged view of axial section of cable tie.

The upper portion of one form of the oral device in accordance with the present invention defines a trough for receiving some of the upper teeth. Once inserted into the mouth the device snugly engages the upper teeth, particularly the front teeth, and remains positioned independent of natural motions of the lower jaw. This trough forms a practical anchor point for attachment of a face mask for receiving ventilation of breathing air by means of a ventilator machine and tube.

Some embodiments of the invention include a lower portion that defines a ramp structure whereby natural jaw motion results in the engagement of the lower teeth with the ramp, which will cam the lower jaw into a more forward position. This action acts to help keep the airway open, thereby, allowing the attached ventilator mask to operate more effectively.

An adjustable fastener system similar to that described above connects the mask to the oral device. The adjustment feature allows the mask to be moved closer or further from the face until the mask seal is in the ideal position as desired. This feature allows the mask portion to be fitted to the patient without the need for straps or other uncomfortable headgear.

Most embodiments of the present invention utilize a mouthpiece of the general type that is referred to in the dental industry as a "boil and bite" oral appliance. Such devices include, but are not limited to, anti-snoring medical oral appliances as described in U.S. Pat. Nos. 5,092,346 and 5,277,202. The disclosures therein are incorporated by reference.

Such oral or anti-snoring appliances are also referred to as mandible repositioning devices and act to keep the airway open during sleep. The appliance is heated and custom molded directly to the patients teeth. The upper trough of the appliance forms a very stable anchor point that holds it securely in place. This stable anchor feature not only holds the mouthpiece in place but becomes the central anchor point for holding the mask against the patients nose and mouth. With the flip of the tongue, or pulling down on the mouthpiece it can be instantly released by the patient or hospital staff.

The present invention substantially combines an oral appliance with a full face mask. A preferred form of the mask is the Respironics, Inc. PerformaTrak full face mask #1012572. A full face mask is preferred because the patient may breathe through his or her nose or mouth or a combination of the two. An adjustable fastener joins the mouthpiece to the mask. Not only does this invention act to help keep the airway open it also eliminates the need for all of the prior art straps and headgear. The combination ventilating mask and dental orthosis is particularly advantageous for use in the treatment of respiratory assistance for patients with snoring and or obstructive sleep apnea. The upper portion of the oral device defines a trough for receiving some of the upper teeth. Once inserted into the mouth the device snugly engages the upper teeth, particularly the front teeth, and remains positioned independent of natural motions of the lower jaw. This trough forms a practical anchor point for attachment of a face mask for receiving ventilation or breathing air by means of a ventilation machine.

The substantial improvements include an adjustable connection method between the mask and mouthpiece. The adjustable connection allows for external adjustment of the tightness of the mask against the patient's mouth and face by using the mouthpiece as an anchor point. In other words, the adjustment feature allows the mask to be moved closer or further from the face until the ideal position is desired. This not only helps keep the airway open but also eliminates the need for bulky and uncomfortable headgear.

This invention consists of three primary parts that are connected to a ventilation machine by others. The ventilation machine provides the proper amount of breathing air supply and control. It contains necessary alarms and tubing.

The invention components include the mouthpiece, adjustment assembly and face mask. These may be factory provided in one single assembled unit or provided as a kit so it can be simply connected to most of the conventional face masks available on the market. In this latter case, the straps and headgear would be removed. Existing masks come in numerous sizes, shapes, and a variety of types. Most have straps and headgear in common. Thus, it is clear that other masks can be utilized with the present invention.

Mouthpiece: The mouthpiece is sometimes referred to as a, "boil and bite" oral appliance in the dental industry.

Adjustment assembly: The adjustment assembly includes all components necessary for connecting the mouthpiece to the full face mask. The preferred adjustment components may include an extension from the mouthpiece, in the form of a releasable type, nylon cable tie fastener. Representative prior art includes fasteners manufactured by 3M Company, 3M Center, St. Paul, Minn. 55144-1000.

The fastener in acordance with the present invention includes an elongated member, a ratchet releasable lock and a quick release lever of the type known in the art. This fastener is secured to the mask whereby the tie is tightened by simply pulling on the end of the tie. To release, it is only necessary to depress the quick release lever. The tie is flexible and allows for off-sets to occur between the mask and mouthpiece while it keeps the seal of the mask snugly fitted to the patients face. The end of the elongated member is dimensioned so that it does not extend substantially farther into the mouth of the user than the mouthpiece. In other certain variations a screw, bushing and adjustment knob may be used to accomplish the adjustment feature.

The masks used may be of a number of sizes and shapes but the preferred type is considered the full face mask. This is usually a clear plastic mask that covers the nose and mouth and has a tube for connection to a ventilator. The mask usually contains a soft sealing portion that fits snugly against the patient's face. Some masks have an air filled chamber seal that easily deforms to the patients' face to obtain a tight fit. The prior art apparatus requires the nurse or respiratory therapist to hold the mask in place with several straps along with other complicated headgearas shown in FIG. 4. These cumbersome straps and headgear are not used with this invention.

Figure 1:
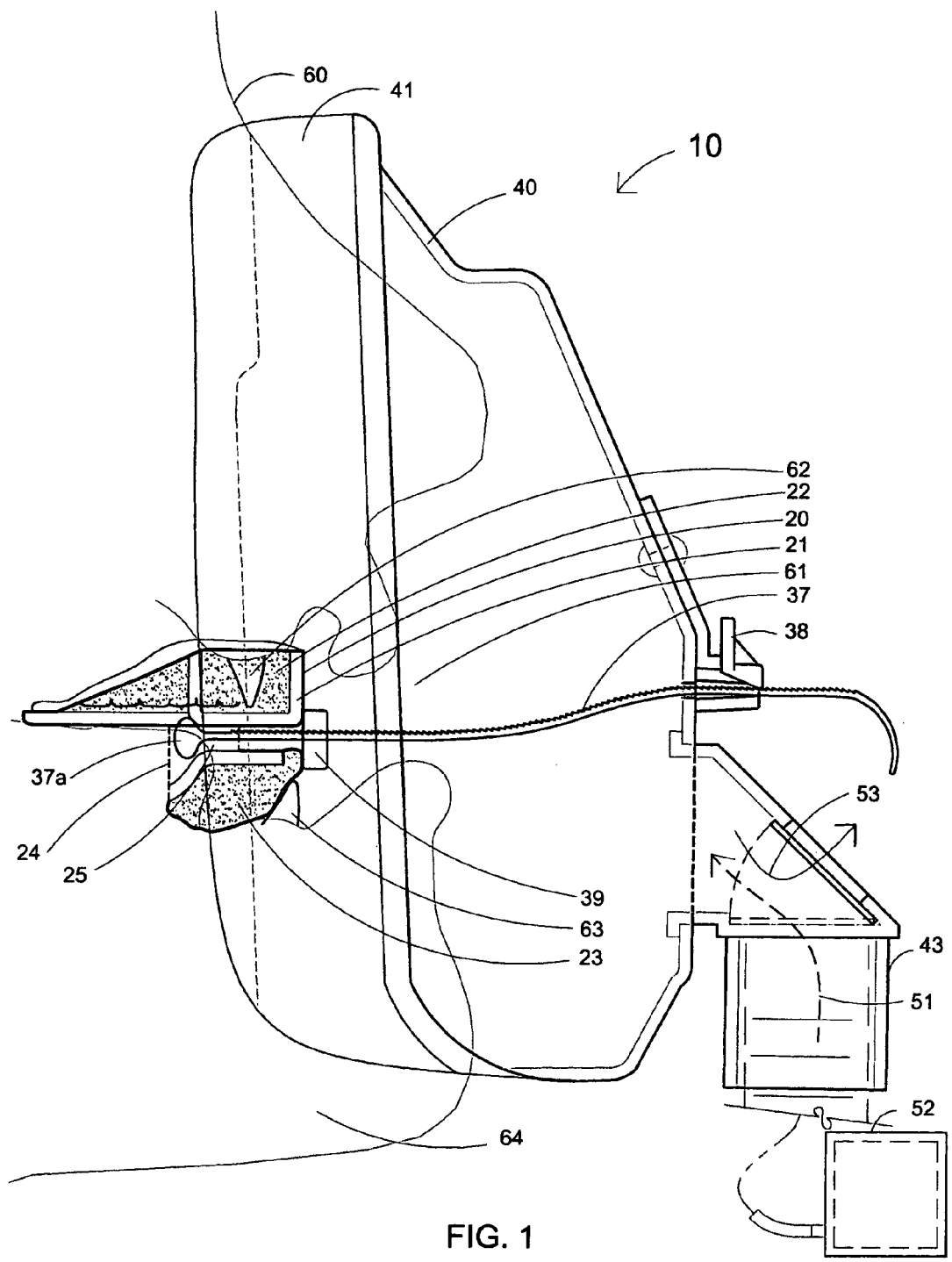
FIG. 1 shows a schematic view of the invention with a quick release nylon tie.

Referring now to FIGS. 1, 2, and 3 there is shown a mouthpiece mask 10 that includes a mouthpiece 20. This embodiment is for patients that have snoring and/or obstructive sleep apnea syndrome. The mandible repositioning type mouthpiece is constructed in accordance with the teachings of U.S. Pat. Nos. 5,092,346 and 5,277,202. The mouthpiece has a preformed upper tray, which in the preferred embodiment is made of Lexan, and a moldable fill material, which in the preferred embodiment is made of Elvax, disposed in the tray or trough 22. This type is commonly considered a boil &bite mouthpiece. The mouthpiece 20 is preferably similar to the anti-snoring appliances described in U.S. Pat. Nos. 5,092,346 and 5,277,202. The mouthpiece 20 in the preferred embodiment is made with a polycarbonate shell such as that sold by General Electric and identified by the trademark Lexan. This mouthpiece 20 includes a trough 22 dimensioned configured for engagement with the user's upper teeth 62 and a support portion and ramp 23 dimensioned and configured for engagement with the user's bottom teeth 63. A softer moldable material fills the trough 22 and covers the ramp 23 portion. In the preferred embodiment this softer material is a moldable material and is manufactured of copolymer and terpolymer resins are available from DuPont and identified by the trademark Elvax. The device is fitted directly to the patient 60 without the need for any laboratory work or molds for teeth impressions. The mouthpiece 20 may, in one form of the invention, have an integral connection port or fastening method for receiving the adjustment assembly that includes a cable tie 37 with locking ridges and a free end and a Quick release lever lock 38. The end of the tie 37 remote from the free end has a smooth shaped head or bulbous end 37a that is larger than the opening 25 in the mouthpiece to prevent it from being pulled through the mouthpiece. The entire cable tie is made of nylon. The quick release lever lock 38 includes a release lever that allows the free end of the cable tie to be moved when release lever is depressed. The quick release lever lock 38 has a short tab that allows it to be riveted or fastened to the mask. The quick release lever lock 38 is positioned in line with a hole 44 in the mask to allow the cable tie 37 end to pass through the mask and through the quick release lever lock 38. The quick release lever lock 38 allows the free end of cable tie 37 to pass through and thus allow for exterior adjustment to be made for tightening or loosening the mask with respect to the mouthpiece. The fastener also includes a slip on lock 39 for securing the cable tie to mouthpiece. This lock 39 is made of nylon and has an opening to allow the tie to slip through but prevents the tie from moving back in the opposite direction. This slip lock 39 may include a release lever for removal.

The mouthpiece 20 is designed to custom fit one patient 60 and is durable and long lasting. Once custom fit for one patient 60 it cannot be used for any other patient. It may be discarded when the patient 60 no longer uses the ventilator 52 and mask 40. Once the patient 60 is custom fitted with the mouthpiece 20 it only takes a few seconds for the patient 60 or medical staff to place it in the patient's mouth 61 for use.

The geometric relationships between the patient and the apparatus are best seen in FIG. 3 which illustrates the head and face of a patient 60, palate 66, tongue 65, oral anti snoring device 20, mouth of patient 61, mask assembly, clear plastic mask assembly 40, quick lock release lever lock 38, cable tie with locking ridges and a free end 37, upper teeth 62 lower teeth 63, lower jaw 64, tongue 65, palate 66, uvula 67, trachea 68 and esophagus 69.

The mouthpiece mask includes an adjustment assembly 37. The adjustment assembly 37 is preferably made of Nylon or another FDA approved material for medical use. The adjustable fastener may includes a relesable nylon cable tie 37 secured by an attachment 39 to the mouthpiece 20 as best seen in FIG. 1. Releasable cable ties are manufactured and sold by a number of business entities. The opposite end of the tie 37 extends through a quick release lever 38 that is bonded to the mask 40. This type adjustment is simple to use, easy to manufacture, inexpensive, easy to clean and can be rapidly adjusted and released.

The attachment 39 may be achieved by bonding, welding, snap-on connection, a clamp, a screw, or other means secured to the mouthpiece 20. Likewise the quick connect lever 38 portion may be bonded, screwed or otherwise secured to the mask 40.

Figure 5:
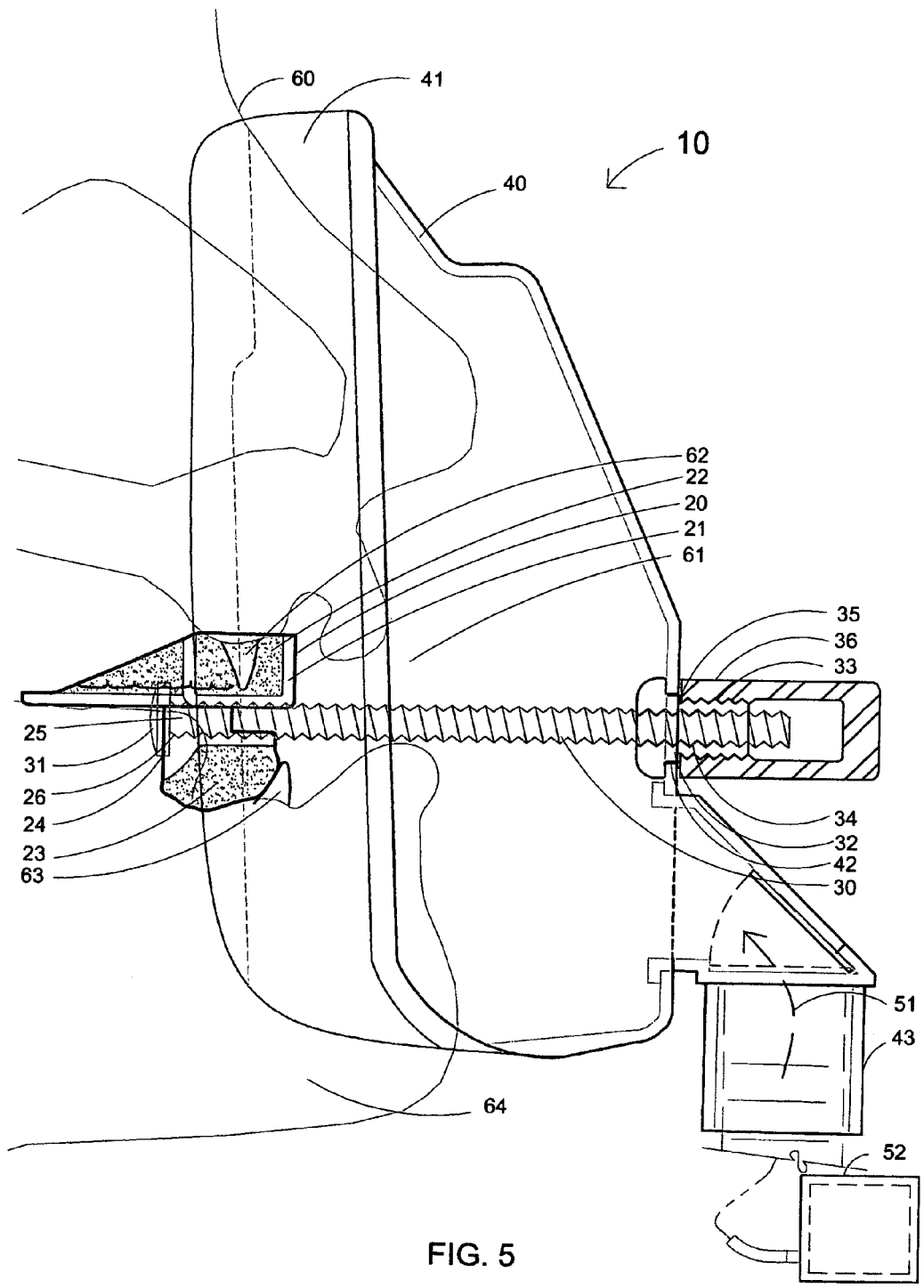
FIG. 5 shows a schematic view of an alternate screw adjustment type method.

Referring now to FIG. 5 there are shown an alternate embodiment of the adjustment assembly in which a screw 30 portion may have a slotted head 31 for secure attachment to the mouthpiece 20 as best shown in FIG. 5. The mouthpiece 20 may have a threaded opening located between the upper trough 22 and the lower ramp 23. The threaded screw 30 is secured to the mouthpiece 20. The shoulder 35 of threaded bushing 33 protrudes though an opening in the mask 40. A knob 36 outside the mask 40 is securely fastened to the bushing 33. By turning the knob 36 close-wise, the screw 33 travels inside the bushing threads 34 and causes the mask 40 and mouthpiece 20 to come closer together. The knob 36 is tightened until a comfortable mask 40 fit and seal 41 is realized. When the knob 36 is turned counter-clock-wise the mask 40 and mouthpiece 20 move further apart.

In another form of the invention a semi-flexible section is placed in line with the adjustment fastener. This would allow for an offset to occur thereby, allowing the mouthpiece to fit securely without undue stress of strain that could act to dislodge the upper trough of the mouthpiece from the upper teeth.

In another form of the invention a smooth rod is used in lieu of a screw. The rod extends through a smooth bore bushing that extends through the mask. Adjustments would be made simply by sliding the mask over the rod and tightening a knob onto the bushing. A soft gasket between the bushing and knob is tightened against the rod to lock it in place. In another form of the invention a portion of the adjustable fastener may include a stretchable portion to help keep the mask in continuous tension. This would help maintain a snug fit as the patients face surface changes during normal activities. Other forms and methods of accomplishing the attachment, adjustment and offset between mouthpiece and mask are also contemplated by the present invention.

The mask 40 as shown in FIG. 1 is of a full face type that covers the nose and mouth. This type allows for breathing to occur through the nose and/or mouth. The mouth 61 may also be "open" or "closed". The mask 40 has a 15 to 22 mm connection port for attachment to an air tube for breathing air 51, and a ventilator machine 52. Various attachment may be provided with the mask 40 and include ports or connections for supplemental oxygen, other gases, mixtures or vapors. In certain variations or for certain patients 60 a safety strap or straps may be necessary to hold the mask and attachments in place.

Figure 6:
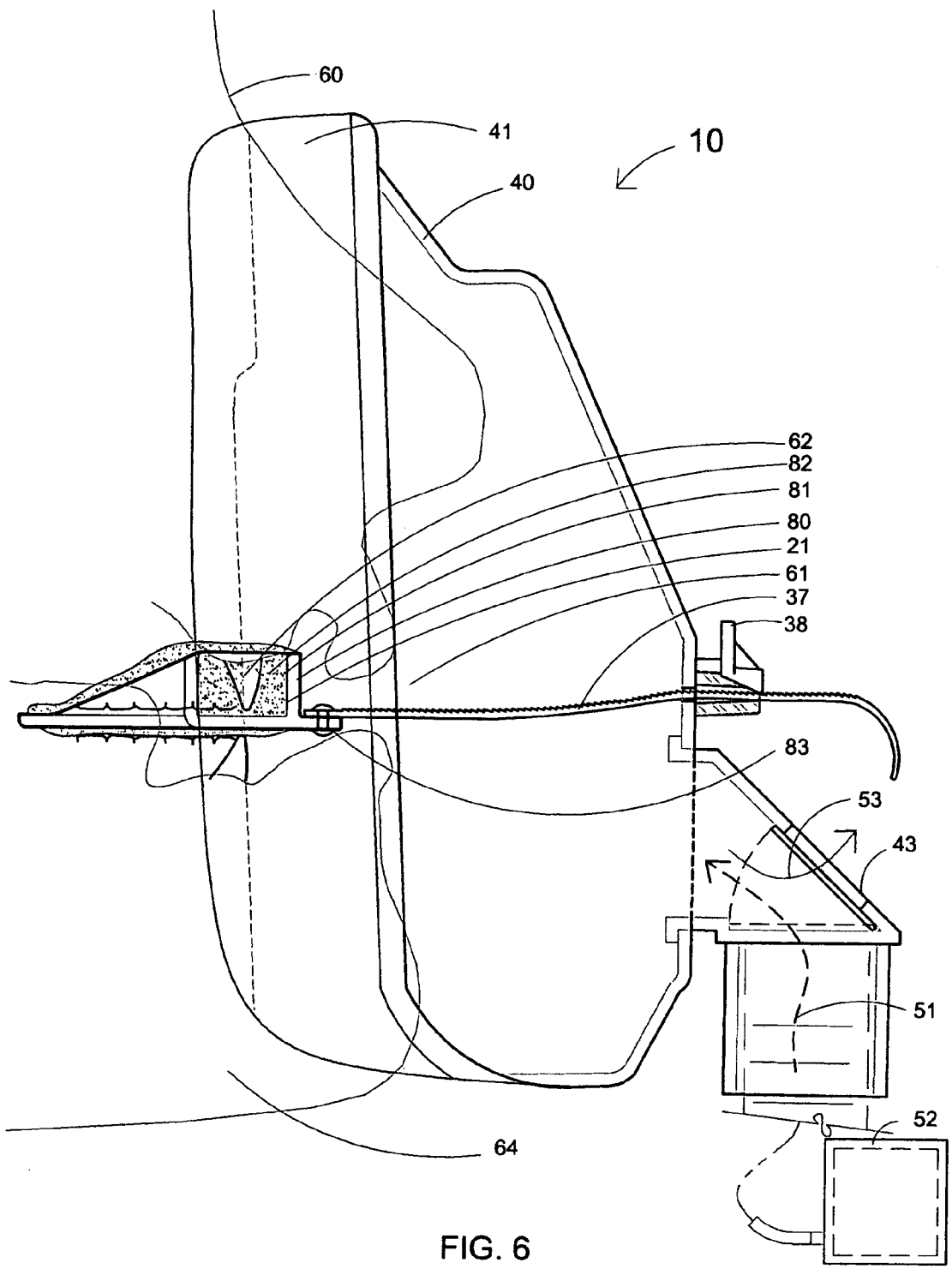
FIG. 6 illustrates apparatus for patients that have nighttime teeth grinding or bruxism; a preformed upper tray, made of Lexan, has a moldable fill material made of Elvax as in U.S. Pat. No. 5,277,203. This is commonly considered a boil & bite type mouthpiece or night guard.
Figure 7:
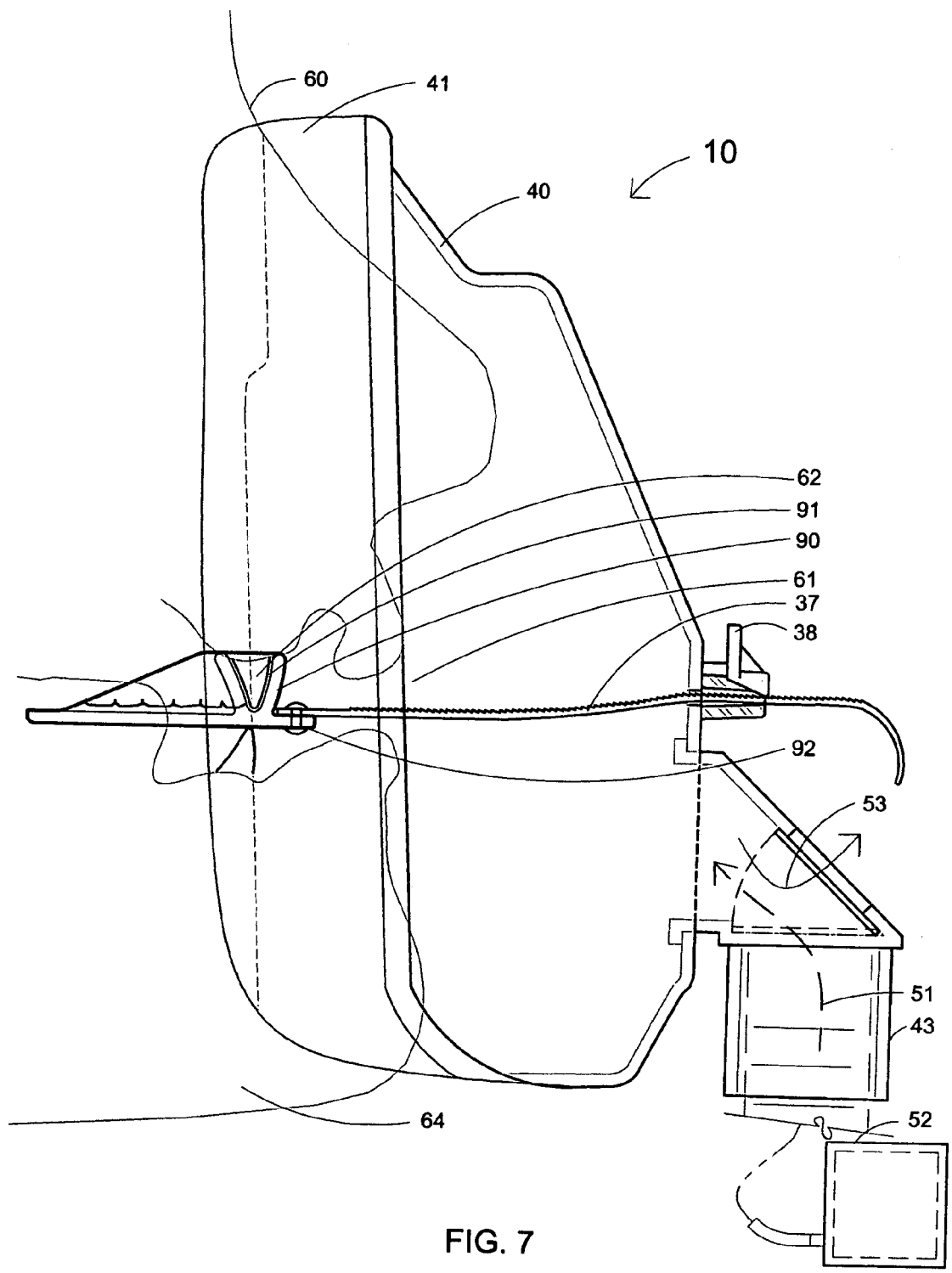
FIG. 7 illustrates apparatus for patients that do not need any anti-snoring or anti teeth grinding devices.

FIG. 4 shows a prior art ventilator mask with a patient. The lower jaw is not moved forward. FIG. 6 illustrates apparatus for patients that have nighttime teeth grinding or bruxism; a preformed upper tray, made of Lexan, has a moldable fill material made of Elvax as in U.S. Pat. No. 5,277,203. This is commonly considered a boil & bite type mouthpiece or night guard. FIG. 7 illustrates apparatus for patients that do not need any anti-snoring or anti teeth grinding devices.

In accordance with present invention the apparatus is fitted to a patient in the following manner:

1. The patient's normal bite is inspected by the doctor. The doctor then asks the patient to swallow as that tends to align the lower jaw. The doctor then asks the patient to move the lower jaw or mandible slightly forward of the normal bite. This may be 2 to 6 millimeters and is determined by the doctor. The patient is then asked to practice biting down several times with the jaw advanced in this forward position. When the mandible is moved slightly forward the tongue reflex is to move forward. This in turn helps keep the airway in a more open position.

2. A cup of water is brought to a boil in a microwave or water heater and then removed from heat. The oral mouthpiece portion of the device is placed in the cup of hot water for 3 minutes. The oral device is then removed from the hot water and allowed to air cool for 25 seconds. This prevents burning the patient.

3. The oral device is then fitted to the upper teeth. The patient is then asked to bite down on the ramp with the jaw in a slightly forward position as practiced. The device is removed after approximately 30 seconds and placed in cool water. Any excess material from the impression is cut away and polished with an acrylic burr.

4. When the patient is ready to receive ventilated air the mouthpiece is re-inserted into the patient's mouth as shown in FIG. 2. The tie end is inserted through the quick release lever on the mask.

5. The tie end is pulled snugly to ensure a tight mask seal as shown in FIG. 3.

6. In another variation of the invention where a screw type adjustment is used as shown in FIG. 5, the screw end with bushing is facing away from the patient mouth.

7. The threaded portion of the bushing passes through a hole in the mask portion and the knob is screwed onto the bushing. This allows the knob and bushing to be turned from outside the mask. When the bushing is turned it moves along the anchored screw. This causes the mask to move away from or toward the patients face. The bushing is inserted through the mask opening and the adjustment knob is locked in place.

8. The adjustment knob is tightened until the mask is snugly fitted to the patient.

9. The air tubing from the ventilator is then connected to the mask tube connector fitting.

10. The ventilator unit is energized and airflow calibrated and set per manufacturers instructions. That completes the basic fitting process of the device.

Once fitted with this invention the patient then has a preferred system that helps insure that the airway remains open. This reduces the unnecessary alarms that are activated when too little air reaches the patients lungs. This help free up the medical staff for other duties.

Each day the device can be removed and washed in warm soap and water and or placed in a denture cleaning solution such as Polident for maintaining it clean and fresh. When not in use it should be cleaned, dried and stored for later use.

For long term users of the device or those with loose teeth or weak gums, it may be necessary to provide a supplemental retainer to prevent teeth eruptions or teeth migration. With most oral appliance, when constant forces are applied to teeth they may in turn migrate or move in the direction of the force. Patients that use any oral appliances should be checked by a dentist on a regular basis.

In another variation of the invention, the soft moldable material referred to herein by the trademark Elvax may be of another material that deforms at very low temperatures or without the use of any hot water. This would be preferred for short term use patients and those that may be in a coma like state. This would allow for near instant fitting of the device which is preferred in any emergency type situations requiring instant fitting.

Other forms of the present invention utilize an engagement member, trough or tray for engaging either the upper teeth or the lower teeth of the user. Ordinarily, the upper teeth are preferred because there is less movement. The entire trough for the upper (or lower) teeth is made with a heat formable plastic or polymer. This type tray is, manufactured in a preformed shape so that one size can be used to fit most patients. It is made from a clear polymer and is molded by heating it in warm water and then placing it in the mouth to form a snug mold directly to the upper teeth. The heated plastic will stretch and or shrink during the molding process to provide a snug fit.

U.S. Pat. No. 5,092,346 describes in detail the manner of construction of such a device for engagement with the upper case of the user. The apparatus described in this patent includes a ramp structure that has the function of inducing the lower jaw and come to a more forward position resulting in a more open posterior airway in the user. As indicated above some forms of the present invention will include such a ramp, such embodiments will have primary application for users with posterior airway obstruction. Other forms of the present invention will not include the ramp; such embodiments will have primary application for users that do not have posterior airway obstruction. Such an embodiment is illustrated in FIG. 7. While boil and bite approaches are particulary effective to produce a snug fit of the appliance on the teeth of the user it will be understood that other embodiments may rely on compounds that engage the teeth without being heated. Compounds similar to the compound used to take dental impressions could also be used, particularly with subsequent baking steps.

The present invention has application to many hospital or home care patients with respiratory, snoring, obstructive sleep apnea, nighttime teeth grinding or bruxism as in U.S. Pat. No. 5,277,203 and/or other breathing related problems. These include short term and long term care, accident patients, severe post polio patients, elderly, critical care, and emergency care patients. Other applications include sleep clinics where patients are tested for various sleep related and breathing problems.

The device may be used by individuals at home with simple snoring or mild obstructive sleep apnea problems. The device could be provided with a readily available ventilator such as that used with a CPAP machine. The device in another form of the invention may have the adjustment assembly removable so the unit may be used with or without a mask and ventilator as necessary. Some patients may only need the use of a ventilator during certain periods and could simply attach the adjustment feature as required.

FIG. 4 shows a patient with prior art ventilator mask held in place with head straps. The straps allow for adjustments of the tightness of mask against the face. The lower jaw is in a normal position.

FIG. 6 illustrates apparatus for patients that have nighttime teeth grinding or bruxism; a preformed upper tray, made of Lexan, has a moldable fill material made of Elvax as described in patent USD Pat. No. 5,277,203. This is commonly considered a boil & bite type mouthpiece or night guard. A quick release nylon tie is shown attached to the night guard and the quick release lever lock that is attached to the mask. This allows for adjustment of the tightness of mask against the face without the need for head straps.

FIG. 7 illustrates apparatus for patients that do not have need any anti-snoring or anti teeth grinding devices. A preformed upper tray engages a plurality of teeth of the patient. A quick release nylon tie is shown attached to the night guard and a quick release lever lock that is attached to the mask. This allows for adjustment of the tightness of the mask against face without the need for head straps.

The present invention has the following advantages over the prior:

1. It acts to reduce the effect or impact of any excess tissue in the back of the throat, thereby, helping to keep the patient's airway open for improved respiratory ventilation.

2. The elimination for the need for bulky and uncomfortable straps and head gear allow for more patient comfort.

3. The device can be used with most existing types of ventilator masks.

4. The device is small, comfortable and easy to fit.

5. Based on previous studies the device helps reduce snoring in over 90% of patients.

6. The device prevents upper and lower teeth contact, thereby preventing teeth grinding and bruxism.

7. Once the patient is custom fitted with the device, in about 10 minutes, the mouthpiece can then be installed or removed in seconds.

8. The use of this invention will lower medical cost substantially by freeing up medical support staff from adjustments and re-adjustments of straps and headgear. In addition, with this improved breathing method there will be less monitoring and alarm activation occurrences.

Although the present invention has been shown and described in terms of the preferred embodiments it will be understood that this invention may include many different face masks and accessories to prevent air leakage from the nose and mouth. Other variations that also accomplish the intent of this invention shall be included. One variation includes an adjustable type that allows for slight adjustment of the mandible without re-heating. This may be accomplished with the placement of a retainer or with an adjustment feature to advance the lower jaw forward. This may include a screw adjustment, snap adjustment or an added retainer section.

Although the description above contains many specifics, these should not be construed as limiting the scope of the invention, but as merely providing illustrations of some of the presently preferred embodiments of this invention. Thus, the scope of this invention should be determined by the appended claims and their legal equivalents. Therefore, it will be appreciated that the scope of the present invention fully encompasses other embodiments which may become obvious to those skilled in the art, and that the scope of the present invention is accordingly to be limited by the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

Reference Numbers Used in the Drawing 10 mouthpiece mask assembly
20 oral anti snoring device
21 trough, a hard plastic shell (Polycarbonate such as Lexan brand)
22 soft moldable plastic fill for upper teeth (ethylene vinyl acetate copolymer and terpolymer resin material such as Elvax brand, softens at 160F).
23 soft moldable plastic ramp for engaging lower teeth. (ethylene vinyl acetate copolymer and terpolymer resin material such as Elvax brand)
24 hard plastic posts between trough and ramp
25 slot or opening between trough and ramp
26. threaded portion at opening
30 screw, threaded. (Part of adjustable assembly)
31 head of screw, slotted
32 bushing, threaded
33 outside threads of bushing for knob
34 inside threads of bushing for screw travel
35 shoulder or collar of bushing to stop knob
36 knob with textured surface
37 cable tie with locking ridges and a free end
37a shaped head end of cable tie
37 cable tie with locking ridges and a free end
38 quick lock release lever lock
39 slip on lock for securing cable tie to mouthpiece
40 mask assembly, clear plastic
41 cushion surface, soft plastic for a snug fit
42 hole in mask for exterior threads of bushing to pass through
43 connection fitting for tubing from ventilator includes a swivel elbow fitting, a check valve and a vent opening for exhaled air
44 hole in mask for cable tie to pass through 50 tubing from ventilator machine
51 air flow in tube from ventilator machine
52 ventilator machine
53 exhaust or exhaled air
60 patient, head and face
61 mouth of patient
62 upper teeth
63 lower teeth
64 lower jaw
65 tongue
66 palate
67 uvula
68 trachea
69 esophagus
70 existing mask
71 straps
80 oral anti-bruxism device
81 trough, a hard plastic shell. Lexan material
82 soft moldable plastic fill at upper teeth. Elvax material
83 connection tab and fastener for cable tie
90 oral tray for upper teeth
91 trough, a moldable plastic or polymer
92 connection tab and fastener for cable tie
100, 102 blocks of wood
104, 106 bores
108 elongated body
109 head
110 locking channel or slip lock
111 pawl
113 enlarged view of axial section of cable tie

The invention claimed is:

1. Apparatus for supporting an associated ventilation apparatus which comprises:
an engagement member dimensioned and configured for engaging and gripping a plurality of teeth of a user;
an adjustment assembly connecting said engagement member to said associated ventilation apparatus, by an elongated flexible member having a plurality of notches thereon disposed respectively at axially spaced portions of the axial extent of the elongated flexible member, the adjustment assembly being dimensioned so that it does not extend substantially farther into the mouth of the user than the engagement member, whereby, adjustment is achieved by selective engagement with one of said notches, said elongated flexible member transferring all forces between said engagement member and the associated ventilation apparatus, all forces between said engagement member and the associated ventilation apparatus placing an axial portion of said elongated flexible member in tension.

2. The apparatus as described in claim 1 further including a first discrete locking member for holding said elongated flexible member in tension.

3. The apparatus as described in claim 2 further including a second discrete locking member for holding said elongated flexible member in tension.

4. The apparatus as described in claim 2 wherein said first locking member first discrete locking member is releasable.

5. The apparatus as described in claim 1 wherein said elongated flexible member has a bulbous axial extremity limiting axial motion thereof.

6. Ventilation apparatus which comprises:
ventilation apparatus including a mask dimensioned and configured for engagement with a face;
an engagement member dimensioned and configured for engaging and gripping a plurality of teeth of a user;
an adjustment assembly for connecting said engagement member to said ventilation apparatus, said adjustment assembly including an elongated flexible member having a plurality of notches thereon disposed respectively at axially spaced portions of the axial extent of the elongated flexible member, the adjustment assembly being dimensioned so that it does not extend substantially farther into the mouth of the user than the engagement member, whereby, adjustment is achieved by selective engagement with one of said notches, said elongated flexible member transferring all forces between said engagement member and the associated ventilation apparatus, all forces between said engagement member and the associated ventilation apparatus placing an axial portion of said elongated flexible member in tension.

7. The apparatus as described in claim 6 wherein said adjustment assembly further includes a first discrete locking member for holding said elongated flexible member in tension.

8. The apparatus as described in claim 7 further including a second discrete locking member for limiting axial motion thereof.

9. The apparatus as described in claim 7 wherein said first discrete locking member is releasable.

10. The apparatus as described in claim 6 wherein said elongated flexible member has a bulbous axial portion limiting axial movement thereof.

11. The apparatus as described in claim 6 wherein said engagement member includes a ramp dimensioned and configured for mandible positioning.

12. The apparatus as described in claim 6 wherein said engagement member is a boil and bite formed product.

13. The apparatus as described in claim 6 wherein said engagement member is at least partly formed of a polycarbonate resin material.

14. The apparatus as described in claim 6 wherein said engagement member is lined with an ethylene vinyl acetate copolymer and terpolymer resin material.

15. The method for supporting an associated ventilation apparatus which includes:
providing an engagement member for engaging and gripping at least one of a plurality of teeth of a user;
providing an adjustment assembly for connecting said engagement member to said associated ventilation apparatus including providing an elongated flexible member having a plurality of notches disposed respectively at axially spaced portions of the elongated flexible member, the adjustment assembly being dimensioned so that it does not extend substantially farther into the mouth of the user than the engagement member.

16. The method as described in claim 15 further including the step of providing a first discrete locking member.

17. The method as described in claim 15 wherein the step of providing and elongated flexible member includes providing an elongated flexible member having a bulbous axial extremity.

18. The method as described in claim 16 wherein said step of providing a first discrete locking member includes providing a first discrete locking member that is releasable.

19. The method as described in claim 16 further including the step of providing a second discrete locking member.

20. The ventilation method which includes:
providing a mask dimensioned and configured for engagement with a face;
providing an engagement member for engaging and gripping a plurality of teeth of a user;

providing an adjustment assembly for connecting the engagement member to the mask, and the step of providing an adjustment assembly includes providing an elongated flexible member having a plurality of notches thereon disposed respectively at axially spaced portions thereof and transferring substantially all forces between the engagement member and a mask by tension forces in the elongated flexible member, the adjustment assembly being dimensioned so that it does not extend substantially farther into the mouth of the user than the engagement member.

21. The method as described in claim 20 wherein the step of providing an adjustment assembly further includes providing a first discrete locking member that limits axial movement the elongated flexible member.

22. The method as described in claim 21 wherein the step of providing an adjustment assembly further includes providing a second discrete locking member for limiting axial movement of the elongated flexible member.

23. The method as described in claim 20 wherein the step of providing an adjustment assembly includes providing an elongated flexible member that has a bulbous axial extremity for limiting axial movement of the elongated flexible member.

24. The method as described in claim 20 wherein said step of providing an engagement member includes providing a first locking member that is releasable.

25. The method as described in claim 20 wherein the step of providing an engagement member includes providing an engagement member that includes a ramp dimensioned and configured for mandible positioning.

26. The method as described in claim 20 wherein the step of providing an engagement member includes providing an engagement member that is a boil and bite formed product.

27. The method as described in claim 20 wherein the step of providing an engagement member includes providing an engagement member that is is at least partly formed of a polycarbonate resin material.

28. The method as described in claim 20 wherein the step of providing an engagement member includes providing an engagement member that is lined with an ethylene vinyl acetate copolymer and terpolymer resin material.

29. Ventilation apparatus which comprises:

ventilation apparatus including a mask dimensioned and configured for engagement with a face;

an engagement member for engaging and gripping a plurality of teeth of a user;

an adjustment assembly for connecting said engagement member to said ventilation apparatus, said adjustment assembly including means for positioning said mask with respect to said engagement member, the adjustment assembly being dimensioned so that it does not extend substantially farther into the mouth of the user than the engagement member, said adjustment assembly including an elongated flexible member having a plurality of notches each disposed at respective axially spaced portions of said elongated member whereby one of said plurality of notches may be selectively utilized to position said mask.

* * * * *